(12) United States Patent
McNeal et al.

(10) Patent No.: US 7,126,732 B2
(45) Date of Patent: Oct. 24, 2006

(54) LENS STRUCTURES, GOGGLES EMPLOYING SAME, METHODS OF FORMING SAME, AND MACHINE PROGRAMMED FOR FORMING SAME

(75) Inventors: Joseph R. McNeal, Hailey, ID (US); Mike Reeves, Woodinville, WA (US); Robert A. Starr, Auburn, WA (US)

(73) Assignee: Smith Sport Optics, Inc., Ketchum, ID (US)

( * ) Notice: Subject to any disclaimer, the term of this patent is extended or adjusted under 35 U.S.C. 154(b) by 0 days.

(21) Appl. No.: 10/903,244

(22) Filed: Jul. 29, 2004

(65) Prior Publication Data

US 2006/0023322 A1    Feb. 2, 2006

(51) Int. Cl.
  *G02C 7/02* (2006.01)
  *G02C 1/00* (2006.01)
(52) U.S. Cl. .......................................... 359/159; 359/43
(58) Field of Classification Search ............ 351/43–45, 351/159, 177; 2/426–435
  See application file for complete search history.

(56) References Cited

U.S. PATENT DOCUMENTS

| 4,373,788 A | * | 2/1983 | Herbert ........................ 351/43 |
| 4,414,693 A | * | 11/1983 | Brody ............................ 2/435 |
| 5,018,223 A | * | 5/1991 | Dawson et al. ................ 2/436 |
| 5,162,825 A | * | 11/1992 | Kamekura et al. .......... 351/163 |
| 5,319,397 A | * | 6/1994 | Ryden .......................... 351/62 |
| 6,637,877 B1 | * | 10/2003 | Hartley et al. ................ 351/44 |
| 6,705,719 B1 | | 3/2004 | Grau et al. .................... 351/41 |
| 2003/0019017 A1 | | 1/2003 | Grau et al. .................... 2/435 |

OTHER PUBLICATIONS

Method of Forming Spacer Used in Goggle Thermal Lens.

* cited by examiner

*Primary Examiner*—Ricky Mack
*Assistant Examiner*—M. Hasan
(74) *Attorney, Agent, or Firm*—Dorsey & Whitney, LLP

(57) ABSTRACT

Lens structures are disclosed. The lens structures include a first lens spaced apart from a second lens and a spacer disposed therebetween comprising an extruded adhesive. Goggles utilizing the lens structures are disclosed. Methods of forming lens structures and goggles are also disclosed. The methods of forming the lens structures include providing a first lens, selectively applying adhesive to a surface of the first lens, contacting the adhesive applied to the first lens with a second lens to form a lens structure, and at least partially curing the adhesive. Lens structures so formed may be attached to a goggle frame. Programmable machines for implementing such inventive methods are also disclosed.

26 Claims, 3 Drawing Sheets

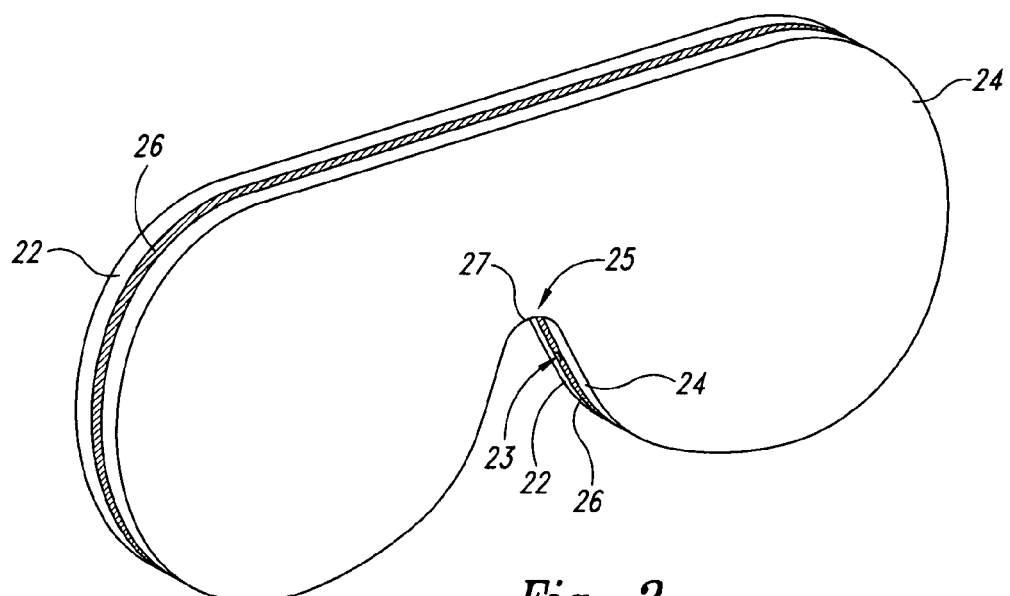
Fig. 3
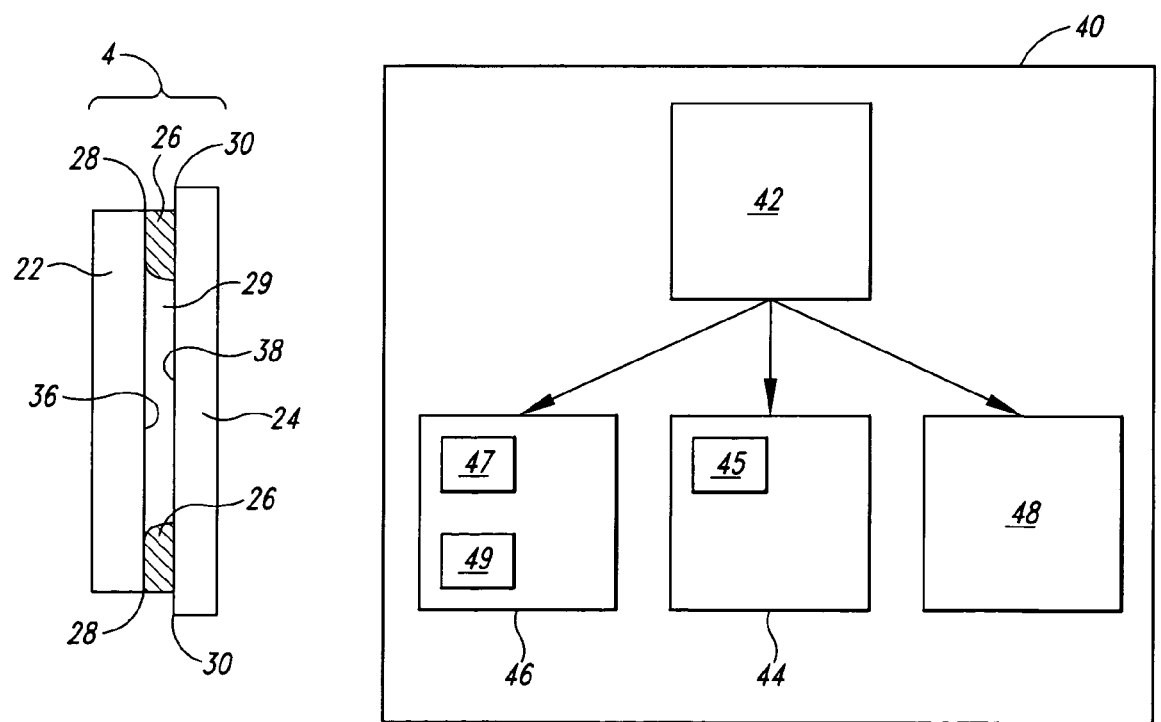
Fig. 4
Fig. 5

LENS STRUCTURES, GOGGLES EMPLOYING SAME, METHODS OF FORMING SAME, AND MACHINE PROGRAMMED FOR FORMING SAME

TECHNICAL FIELD

The present invention relates to lens structures, goggles employing the lens structures, and methods of forming lens structures. The present invention also includes programmable machines for implementing the methods of forming the lens structures.

BACKGROUND OF THE INVENTION

Flexible goggles having a flexible housing in which a lens structure is mounted are well known. Individuals often wear such goggles to protect their eyes or to improve their vision when participating in a sport or a recreational activity, such as skiing or motorcycle racing. Such goggles are commonly used by skiers or motorcyclists to protect their eyes from wind and precipitation.

Goggles are shaped to fit flush against the contours of the human face. When worn by a user, a generally closed chamber is defined between the goggle's lens structure and the wearer's face. As time passes, moisture evaporating from the wearer's face increases the relative humidity of the air in the chamber. As the relative humidity increases, so does the dew point, or the point at which water molecules will condense from a vapor phase to a liquid phase. When cold air surrounding the goggle reduces the temperature of the lens structure of the goggle to a temperature below the dew point, water condenses on the inner surface of the lens structure. The condensate on the inner surface of the lens structure decreases the wearer's vision and makes it more difficult, or impossible, for the wearer to participate in the sport or recreational activity.

One technique for reducing condensation in the chamber is by using a double-paned lens structure to insulate the internal surface of the lens structure from the cold, external temperature. One conventional double-paned lens structure is referred to as a "thermal lens" and is formed of an inner lens and an outer lens. The inner and outer lenses are assembled and spaced in parallel relation by a spacer. The spacer is typically made of closed cell, flexible foam which is bonded to the inner and outer lenses in a fashion so as to seal against both.

One conventional method of forming the spacer is by die cutting a sheet of flexible foam material having a pressure sensitive adhesive bonded to each side thereof to define the shape of the spacer. After die cutting, the formed spacer is manually applied to one of the lenses followed by bonding the other lens to form a double-paned lens structure. However, the die cutting process wastes material because only a portion of the sheet is required to form the spacer. Also, manually applying the die cut spacer is tedious, time consuming, and prone to positioning errors that reduce the quality of the resulting product. Furthermore, spacers formed of flexible foam type materials are subject to delaminating from the lenses, resulting in fogging of the lens structures.

Another conventional method for forming the spacer is by injection molding a plastic spacer onto a first lens. During this process, the plastic is injected into a die that defines the shape of the spacer and upon curing the plastic bonds to the first lens. The injection molding process requires a die that is specifically designed for the particular lens geometry that the spacer is formed on. A second lens is then assembled with the first lens that includes the spacer thereon. The spacer is bonded to the second lens by radio frequency (RF) welding or gluing. Such a method is employed to form the spacer of the double-paned lens structure used in various goggles commercially available from Carrera Sport. However, double-paned lenses formed by this method are very rigid due to the inherent rigidity of the plastic formulation compatible with the injection molding process that is used to form the spacer. The rigidity of the spacer results in a rigid double-paned lens structure that will not adequately form fit to all potential wearer's faces or can cause substantial discomfort to the wearer's face. Furthermore, the die required for injection molding is expensive to fabricate and is specific to a particular lens geometry. Thus, injection molding is not a particularly versatile process for forming the spacer.

Accordingly, there is a need for a method of forming a lens structure by a relatively inexpensive process that produces a lens structure that helps alleviate the problem of condensation in the chamber of the goggle. It would also be desirable that the method for forming the spacer of the lens structure is adaptable to a variety of lens geometries. Furthermore, it would be desirable that the lens structure have the ability to comfortably form fit to the wearer's face.

SUMMARY OF THE INVENTION

In one aspect of the present invention, a lens structure for use in a goggle is disclosed. The lens structure includes a first lens having a first surface and a second lens having a second surface. The first lens and the second lens are spaced apart from each other and positioned with respect each other so that the first surface opposes the second surface. A spacer of an extruded adhesive is disposed between the first surface of the first lens and the second surface of the second lens to define a chamber therebetween.

In another aspect of the present invention, a goggle is disclosed. The goggle includes a frame coupled to a lens structure of the present invention.

In another aspect of the present invention, an exemplary method for forming a lens structure and a goggle is disclosed. The method includes providing a first lens having a surface including a peripheral edge, selectively applying adhesive to the surface of the first lens along a peripheral region thereof, and contacting the adhesive applied to the first lens with a second lens to form a lens structure. The lens structures so formed may be coupled to a goggle frame and additional goggle components, such as a ventilation adjustment assembly, as desired.

In yet another aspect of the present invention, a programmable machine for dispensing adhesive on a lens is disclosed. The programmable machine includes at least one controller and a movable arm in operative communication with the at least one controller. The movable arm is configured to retain the lens and position the lens in a desired orientation. The programmable machine further includes a dispensing system in operative communication with the at least one controller, the dispensing system having at least one dispensing element configured to dispense adhesive. The at least one controller of the programmable machine is programmed to cause the at least one dispensing element to selectively dispense adhesive along a path over the lens.

BRIEF DESCRIPTION OF THE DRAWINGS

FIG. 3 is a perspective view of the lens structure shown in FIG. 1.

FIG. 4 is a sectional view of the lens structure shown in FIGS. 1 and 3.

FIG. 5 is a simplified block diagram of a programmable robotic system suitable for practicing the present invention.

DETAILED DESCRIPTION

The present invention is directed toward lens structures, goggles employing such lens structures, and methods of forming lens structures by selectively applying adhesive on a first lens and bonding the first lens to a second lens. The present invention also includes programmable machines for implementing such methods. Many specific details of certain embodiments of the present invention are set forth in the following description and in FIGS. 1 through 6 in order to provide a thorough understanding of such embodiments. One skilled in the art, however, will understand that the present invention may have additional embodiments, or that the present invention may be practiced without several of the details described in the following description.

Figure 1:
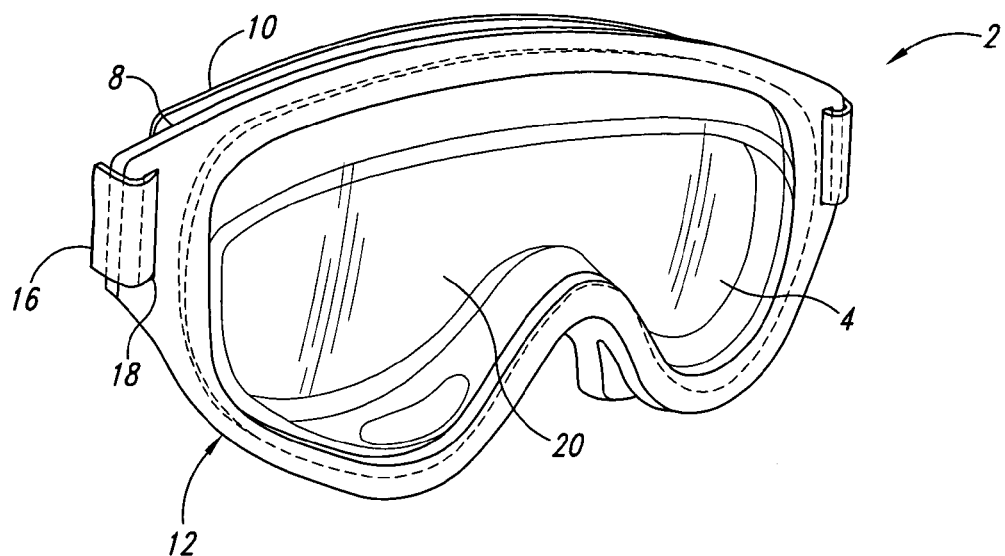
FIG. 1 is a perspective view of a goggle of the present invention.

FIG. 1 depicts a goggle 2 including a lens structure 4. The goggle 2 includes a goggle frame 12 having a generally annular structure and may be molded of one piece from a resilient flexible material such as a soft plastic or soft rubber. A rim 8 for contacting the face of a wearer is lined with a padding 10 of sponge-type material to seal the frame 12 against the wearer's face. The lens structure 4 of flexible transparent material has a peripheral edge which is received within a peripheral groove formed interiorly around a front section 14 of the frame 12. The lens structure 4 may be flat and bent to an arcuate configuration which fits the frame 12, or may be curved and, if desired, form a part of the structural support to maintain the shape of the goggle 2. To secure the goggle 2 to the wearer's head, an elastic strap 16 has folded, stitched ends which are received in slots 18 formed in frame front section 14. A slide buckle (not illustrated) allows for adjustment of the length of the elastic strap 16. The goggle 2 is shaped to fit flush against the contours of the human face. When worn by a user, a generally closed chamber 20 is defined between lens structure 4 and the wearer's face.

Figure 2:
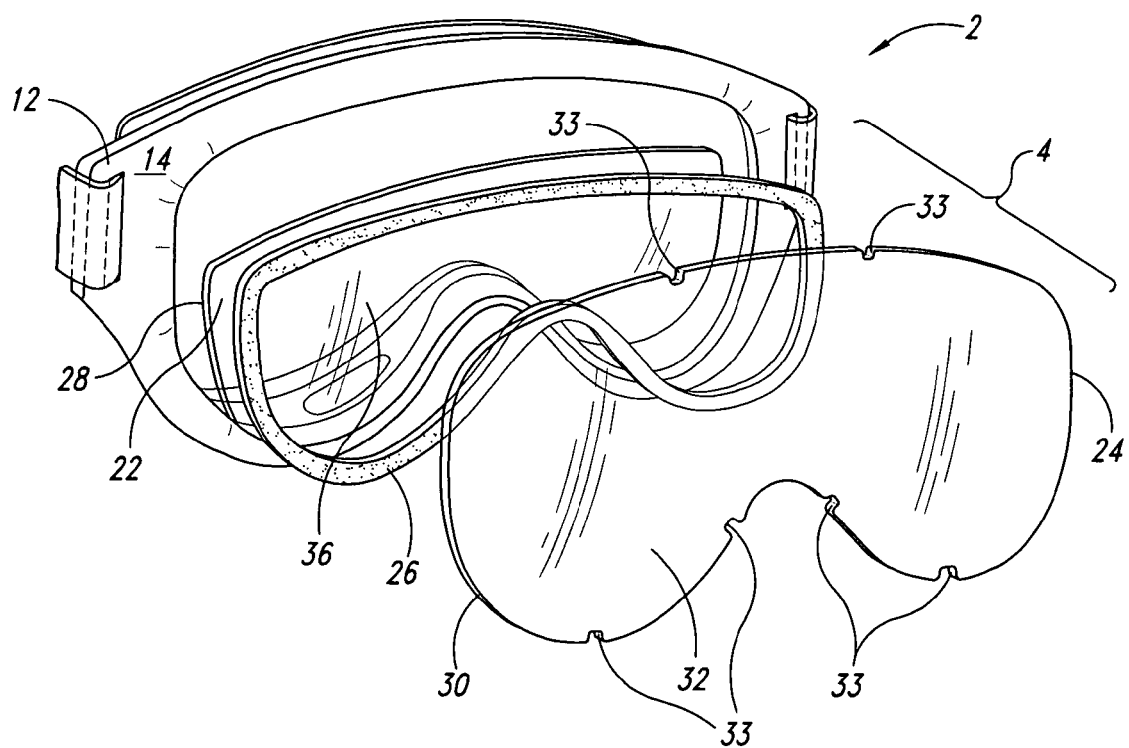
FIG. 2 is an exploded perspective view of the goggle shown in FIG. 1.

Referring to the exploded perspective view of the goggle 2 in FIG. 2, the lens structure 4 is a thermal lens and is formed of an inner lens 22 and an outer lens 24. The lens 22 may be formed from a semirigid plastic material such as cellulose propionate and the lens 24 may be formed from a plastic material such as polycarbonate. The inner lens 22 may also be treated on both sides thereof with an appropriate antifog treatment, as known in the art. The lenses 22 and 24 are assembled and spaced in a substantially parallel relation by a spacer 26. The spacer 26 may be made of an extruded, at least partially cured adhesive material which is bonded to lenses 22 and 24 to define a chamber 29 (not illustrated, see FIG. 4) therebetween. The spacer 26 is located adjacent to peripheral edges 28 and 30 of the lenses 22 and 24, respectively, and extends peripherally thereabout to define the chamber 29 (not illustrated, see FIG. 4) between the lenses 22 and 24. In another embodiment, the spacer 26 may overlie the peripheral edge 28 of the inner lens 22.

As shown in FIG. 3, the spacer 26 may include an aperture 23 that transversely extends through a thickness of the spacer 26 to communicate the ambient pressure surrounding the lens structure 4 with the chamber 29 (not illustrated, see FIG. 4) formed between the lenses 22 and 24. The aperture 23 is located in nose region 25 of the lens structure 4 so that any condensation will desirable flow downwardly from an upper portion 27 of the nose region 25 out of the aperture 23. The aperture 23 is also dimensioned small enough so that moisture, such as from snow and rain, will not pass through the aperture 23 into the chamber 29 from the surroundings. The aperture 23 enables equalizing the pressure between the ambient pressure of the surroundings and the pressure in the chamber 29. The ability to equalize pressure is desirable to prevent the lens structure 4 from bursting due to the pressure inside the chamber 29 being greater than the ambient pressure as would occur if the lens structure 4 was brought from a lower elevation, such as the base of a ski resort, to a higher elevation, such as at the top of the ski resort.

Suitable adhesives for forming the spacer 26 include, but are not limited to, silicone based adhesives and urethane based adhesives. One suitable silicone based adhesive is the GE RTV 5813, which is a one part, moisture curable adhesive that cures to approximately full strength in about twenty-four hours. The GE RTV 5813 is commercially available from the General Electric Corporation. Urethane adhesives may also be used, but typically require two parts and are more expensive than one part adhesives such as the aforementioned GE RTV 5813.

FIG. 4 illustrates a more detailed sectional view of the lens structure 4 and the spacer 26. The inner lens 22 is bonded to the outer lens 24 using a mass of extruded, at least partially cured adhesive which forms the spacer 26. The spacer 26 defines the chamber 29 between the inner lens 22 and the outer lens 24. The spacer 26 extends along a region of a surface 36 adjacent the peripheral edge 28 and a region of a surface 38 adjacent the peripheral edge 30. As shown in FIG. 4, the spacer 26 may overlie the peripheral edge 28 of the surface 36 of the inner lens 22.

The methods of the present invention for forming the goggle 2 having the lens structure 4 will now be discussed with reference to FIGS. 5 through 6. The methods of the present invention may be practiced using a programmable machine 40 for dispensing adhesive on a lens. One suitable programmable machine 40 is the LR Mate 200i commercially available from Fanuc Robotics of Rochester Hills, Mich. FIG. 5 depicts a simplified block diagram of the programmable machine 40 for dispensing adhesive on a lens that includes a controller 42 for effecting a number of different programmable functions, a movable arm 44 that includes a vacuum pickup tool 45 at an end thereof configured to hold a lens or lens structure, and a dispensing system 46. The dispensing system 46 includes a movable arm 47 that is positionable as desired and carries a dispensing element 49 at an end thereof such as, for example, a syringe, a nozzle, or other suitable structure configured to dispense a viscous adhesive. The dispensing system 46 includes a servo motor that may controllably bias a plunger to extrude a predetermined amount of adhesive out of an opening of the dispensing element 49. The programmable machine 40 further includes a movable support 48 configured hold a plurality of trays adapted for holding the inner lens 22 and the outer lens 24 in a desired orientation. The controller 42 may be programmed to cause the movable arm 44, the dispensing system 46, and the movable support 48 to perform a number of different inventive functions, as will be explained in more detail below in the flow diagram of FIG. 6.

Figure 6:
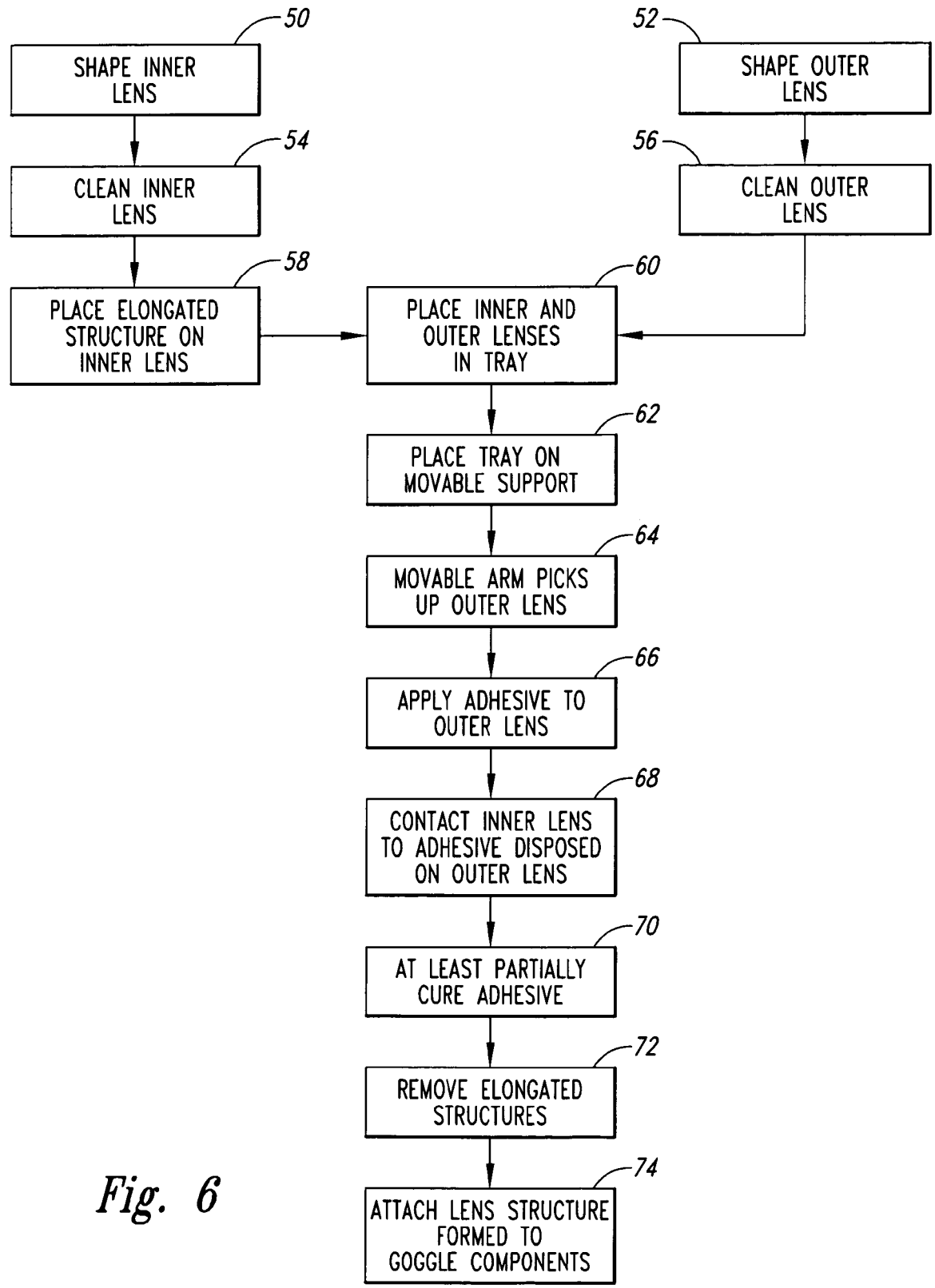
FIG. 6 is a flow diagram describing an exemplary method of forming lens structures and goggles of the present invention.

An exemplary method of forming the goggle 2 having the lens structure 4 is described in the flow diagram of FIG. 6 in conjunction with FIGS. 1 through 5. In act 50, an inner lens 22 is shaped to define the geometry thereof by die cutting a blank formed of a flexible material such as cellulose propionate. Of course other suitable cutting processes may be used to shape the inner lens 22 such as a milling or a shearing process. The inner lens 22 may also be treated prior to die cutting with an appropriate antifog treatment on both sides thereof. In act 52, which may occur before, after, or simultaneously with act 50, an outer lens 24 is shaped from a molded blank (e.g., molded polycarbonate) to define the geometry thereof. The outer lens 24 will typically include grooves or keyholes 33 along the peripheral edge 30 thereof configured to releasably secure the outer lens 24 to the frame 12. One method of shaping the outer lens 24 is by trimming the molded blank using a computer controlled milling machine. After shaping the inner lens 22 in act 50 and the outer lens 24 in act 52, each lens 22 and 24 is respectively cleaned in acts 54 and 56 to prepare the surfaces thereof for adhesive bonding. In act 58, an elongated structure, such as a thin piece of wire or dental floss, may be placed proximate the nose region 25 of the inner lens 22.

In act 60, the lenses 22 and 24 are placed in a tray that has suitable fixtures for supporting each of the lenses 22 and 24 in a desired orientation. The inner lens 22 is supported in the tray with surface 36 upwardly facing and the outer lens 24 is supported in the tray with the surface 38 downwardly facing.

In act 62, the tray may be placed on the movable support 48 that is part of the programmable machine 40. In act 64, the vacuum pickup tool 45 of the movable arm 44 picks up the outer lens 24 situated on the movable support 48 to orient the surface 38 so that adhesive may be dispensed thereon. In act 66, the dispensing element 49 of the dispensing system 46 selectively dispenses a controlled amount of the adhesive on the surface 38 of the outer lens 24. The adhesive may be selectively applied by the dispensing element 49 dispensing a volume of viscous, uncured adhesive along a path adjacent the peripheral edge 30 of the surface 38 of the outer lens 24. By precisely controlling the volume of the adhesive dispensed from the dispensing element 49 and the speed that the dispensing element 49 travels relative to the outer lens 24, the width of the bead of the adhesive dispensed on the surface 38 may be accurately controlled to have a substantially uniform width.

In act 68, the lens structure 4 may be formed by the movable arm 45 positioning and downwardly pressing the outer lens 24 including the adhesive dispensed thereon to contact the surface 36 of the inner lens 22 situated on the movable support 48. The tray placed on the movable support 48, which carries the inner lens 22, includes a fixture configured for retaining the shape of the inner lens 22 while the movable arm 45 downwardly presses the outer lens 24 against it. The inner lens 22 may be contacted with the adhesive disposed on the outer lens 24 so that the adhesive extends along a region adjacent the peripheral edge 28 of the inner lens 22. As previously mentioned, the adhesive may be contacted to the inner lens 22 so that the adhesive overlies the peripheral edge 28. In act 70, the adhesive 59 is at least partially cured to form a strong and flexible spacer 26 bonding the inner lens 22 and the outer lens 24 together to form the lens structure 4, as illustrated in FIGS. 1 through 4. If the adhesive is a silicone based adhesive, such as the aforementioned GE RTV 5813, the adhesive will air cure to approximately full strength. Other adhesives may require heating the lens structure 4 to an elevated temperature, such as with hot air, to effect curing thereof or to decrease the curing time.

Upon contacting the adhesive dispensed onto the outer lens 24 with the inner lens 22 (act 68), the elongated structure is covered by the adhesive and a portion projects outwardly therefrom. In act 72, the elongated structure may be manually removed to form the aperture 23 (See FIG. 3) extending through a thickness of the at least partially cured, adhesive that forms the spacer 26. In act 74, the lens structure 4 formed in accordance with the present invention may be secured to the frame 12 and additional goggle components such as a ventilation adjustment system (not illustrated). Although the above exemplary method in FIG. 6 is described with the adhesive dispensed onto the outer lens 24, the method may also be performed by dispensing the adhesive onto the inner lens 22 followed by contacting the adhesive disposed thereon to the outer lens 24 to form the lens structure 4.

By employing the programmable machine 40, the spacer 26 may be formed on lenses having a variety of different geometries. Thus, the programmable machine 40 and the methods of the present invention for forming the spacer 26 are adaptable for use on almost any type of lens design and versatile compared with conventional injection molding and die cutting technology because a die that is specifically designed and limited for use with a particular lens design is not used. The controller 42 of the programmable machine 40 may be re-programmed to enable forming the spacer 26 on a lens having a different geometry.

Although the present invention has been described with reference to the disclosed embodiments, persons skilled in the art will recognize that changes may be made in form and detail without departing from the spirit and scope of the invention. Such modifications are well within the skill of those ordinarily skilled in the art. Accordingly, the present invention is not limited except as by the appended claims.

What is claimed is:

1. A lens structure for use in a goggle comprising:
   a first lens having a first surface;
   a second lens having a second surface, the second surface opposing and spaced apart from the first surface; and
   a spacer comprising an extruded adhesive disposed between the first surface and the second surface to define a chamber therebetween, the spacer having at least one aperture extending through a thickness thereof to communicate ambient pressure with the chamber.

2. The lens structure of claim 1, wherein the spacer extends along a region adjacent a first peripheral edge of the first surface and a region adjacent a second peripheral edge of the second surface.

3. The lens structure of claim 1, wherein the extruded adhesive overlies a first peripheral edge of the first surface.

4. The lens structure of claim 1, wherein the extruded adhesive is at least partially cured.

5. The lens structure of claim 1, wherein the extruded adhesive comprises silicone.

6. The lens structure of claim 1, wherein the extruded adhesive comprises urethane.

7. A goggle comprising:
   a frame coupled to a lens structure, the lens structure comprising:
   a first lens having a first surface;
   a second lens having a second surface, the second surface opposing and spaced apart from the first surface; and a spacer comprising an extruded adhesive disposed between the first surface and the second surface to define a chamber therebetween, the spacer having at least one aperture extending through a thickness thereof to communicate ambient pressure with the chamber.

8. The lens structure of claim 7, wherein the spacer extends along a region adjacent a first peripheral edge of the first surface and a region adjacent a second peripheral edge of the second surface.

9. The goggle of claim 7, wherein the extruded adhesive overlies a first peripheral edge of the first surface.

10. The goggle of claim 7, wherein the extruded adhesive is at least partially cured.

11. The goggle of claim 7, wherein the extruded adhesive comprises silicone.

12. The goggle of claim 7, wherein the extruded adhesive comprises urethane.

13. A method of forming a lens structure comprising:
providing a first lens having a surface including a peripheral edge;
selectively applying adhesive to the surface of the first lens along a path so that the adhesive overlies the peripheral edge of the first lens;
contacting the adhesive applied to the first lens with a second lens to form the lens structure; and
at least partially curing the adhesive.

14. The method of claim 13, wherein the act of providing a first lens comprises providing a movable arm that retains the first lens, the movable arm moving in response to instructions from at least one controller.

15. The method of claim 13, wherein the act of selectively applying adhesive comprises extruding adhesive onto the surface of the first lens.

16. The method of claim 13, wherein the act of selectively applying adhesive comprises extruding adhesive onto the surface of the first lens from a dispensing element which operates in response to instructions from at least one controller.

17. The method of claim 13, wherein the act of selectively applying an adhesive comprises dispensing adhesive from an opening of a dispensing element.

18. The method of claim 13, wherein the act of contacting the adhesive applied to the first lens comprises downwardly pressing the first lens so that the adhesive thereon contacts the second lens.

19. The method of claim 13, wherein the act of contacting the adhesive applied to the first lens comprises retaining the first lens on a movable arm with a vacuum force and downwardly pressing the first lens so that the adhesive thereon contacts the second lens, the movable arm operating in response to instructions from at least one controller.

20. The method of claim 13, further comprising disposing an elongated structure on a surface of the second lens.

21. The method of claim 20, wherein upon at least partially curing the adhesive, further comprising removing the elongated structure to form an aperture extending through a thickness of the adhesive.

22. The method of claim 20, wherein the act of disposing an elongated structure comprises disposing a piece of wire or fabric.

23. The method of claim 13, wherein the act of selectively applying adhesive comprises applying a silicone adhesive.

24. The method of claim 13, wherein the act of selectively applying adhesive comprises applying a urethane adhesive.

25. The method of claim 13, wherein the first lens is an outer lens of a thermal lens structure and the second lens is an inner lens of the thermal lens structure.

26. The method of claim 13, further comprising attaching the lens structure to a goggle frame.

* * * * *